(12) United States Patent
Beck et al.

(10) Patent No.: US 9,513,242 B2
(45) Date of Patent: Dec. 6, 2016

(54) HUMIDITY SENSOR

(71) Applicant: Honeywell International Inc., Morristown, NJ (US)

(72) Inventors: Scott E. Beck, Murphy, TX (US); Carl Stewart, Plano, TX (US); Richard A. Davis, Plano, TX (US)

(73) Assignee: Honeywell International Inc., Morris Plains, NJ (US)

( * ) Notice: Subject to any disclaimer, the term of this patent is extended or adjusted under 35 U.S.C. 154(b) by 89 days.

(21) Appl. No.: 14/484,821

(22) Filed: Sep. 12, 2014

(65) Prior Publication Data
US 2016/0077028 A1   Mar. 17, 2016

(51) Int. Cl.
*G01N 27/12* (2006.01)
*G01N 27/22* (2006.01)

(52) U.S. Cl.
CPC .......... *G01N 27/128* (2013.01); *G01N 27/121* (2013.01); *G01N 27/225* (2013.01)

(58) Field of Classification Search
CPC .... G01N 27/128; G01N 27/12; G01N 27/121; G01N 27/124; G01N 27/123; G01N 27/223; G01N 27/225
See application file for complete search history.

(56) References Cited

U.S. PATENT DOCUMENTS

| | | |
|---|---|---|
| 4,366,709 A | 1/1983 | Eiermann et al. |
| 4,429,343 A | 1/1984 | Freud |
| 4,564,882 A | 1/1986 | Baxter et al. |
| 5,529,279 A | 6/1996 | Beatty et al. |
| 5,535,633 A | 7/1996 | Kofoed et al. |
| 6,150,681 A | 11/2000 | Allen |
| 6,222,376 B1 | 4/2001 | Tenney, III |
| 6,470,741 B1 | 10/2002 | Fathollahzadeh |

(Continued)

FOREIGN PATENT DOCUMENTS

| | | |
|---|---|---|
| CN | 102213606 | 10/2011 |
| EP | 0981737 B1 | 7/2001 |

(Continued)

OTHER PUBLICATIONS

International Search Report and Written Opinion, PCT/US2015/049185, dated Dec. 17, 2015, 14 pages.

(Continued)

*Primary Examiner* — Blake A Tankersley
(74) *Attorney, Agent, or Firm* — Conley Rose, P.C.; Kristin Jordan Harkins

(57) ABSTRACT

A humidity sensor may include a first substrate having a recess formed in a first side, a second substrate and an insulating layer supported by the second substrate. The second substrate and the insulating layer may be supported by the first side of the first substrate and extend over the recess to form a diaphragm with the insulating layer facing the recess. The diaphragm may be at least partially thermally isolated from a remainder of the second substrate. A resistive heater element may be supported by the diaphragm. A pair of sensing electrodes are electrically separated from each other and supported by the diaphragm. A sensing material is disposed over the pair of sensing electrodes, wherein an electrical property of the sensing material changes in response to a change in moisture content of the sensing material.

16 Claims, 27 Drawing Sheets

(56) References Cited

U.S. PATENT DOCUMENTS

| | | |
|---|---|---|
| 6,615,667 B2 | 9/2003 | Smith |
| 6,658,946 B2 | 12/2003 | Lipscomb et al. |
| 6,690,569 B1 | 2/2004 | Mayer et al. |
| 6,724,612 B2 | 4/2004 | Davis et al. |
| 6,867,602 B2 | 3/2005 | Davis et al. |
| 6,945,123 B1 | 9/2005 | Kuehl et al. |
| 7,111,518 B1 | 9/2006 | Allen et al. |
| 7,233,000 B2 | 6/2007 | Nassiopoulou et al. |
| 7,278,309 B2 | 10/2007 | Dmytriw et al. |
| 7,280,927 B1 | 10/2007 | Dmytriw |
| 7,493,822 B2 | 2/2009 | Stewart et al. |
| 7,563,692 B2 | 7/2009 | Fortin et al. |
| 7,635,091 B2 | 12/2009 | Engler et al. |
| 7,678,600 B2 | 3/2010 | Villa et al. |
| 7,683,636 B2 | 3/2010 | Alimi et al. |
| 7,703,339 B2 | 4/2010 | Sulouff, Jr. et al. |
| 7,710,128 B2 | 5/2010 | Alimi et al. |
| 7,713,772 B2 | 5/2010 | Vanha et al. |
| 7,769,557 B2 | 8/2010 | Bey et al. |
| 7,924,028 B2 | 4/2011 | Alimi et al. |
| 8,047,074 B2 | 11/2011 | Jun et al. |
| 8,104,355 B2 | 1/2012 | Minamitani et al. |
| 8,601,879 B2 | 12/2013 | Okada |
| 8,616,065 B2 | 12/2013 | Stewart et al. |
| 8,975,671 B2 | 3/2015 | Ten Have |
| 9,080,907 B2 | 7/2015 | Haneef et al. |
| 2007/0251292 A1* | 11/2007 | Beck .................. G01F 1/6845 73/1.35 |
| 2008/0134753 A1* | 6/2008 | Jun .................. G01N 27/128 73/23.2 |
| 2010/0140669 A1 | 6/2010 | Xie |
| 2011/0107832 A1 | 5/2011 | Sakuma |
| 2011/0252882 A1 | 10/2011 | Beck et al. |
| 2012/0205653 A1 | 8/2012 | Nishikage et al. |
| 2013/0001710 A1 | 1/2013 | Daneman et al. |
| 2013/0139584 A1 | 6/2013 | Qasimi et al. |
| 2014/0073927 A1 | 3/2014 | Chung |
| 2014/0210036 A1 | 7/2014 | Sunier et al. |
| 2014/0298913 A1 | 10/2014 | Stewart et al. |
| 2015/0021716 A1* | 1/2015 | Lee .................. G01N 27/128 257/414 |

FOREIGN PATENT DOCUMENTS

| | | |
|---|---|---|
| JP | 2009050376 A | 3/2009 |
| KR | 1020050076524 A | 7/2005 |
| WO | WO 2010/033358 | 3/2010 |

OTHER PUBLICATIONS

Lee, "Fabrication and Sensing Properties of a Micro-Humidity Sensor System Using CMOS Technology," Electronic Materials Letters, vol. 6, No. 1, pp. 7-12, Mar. 31, 2010.

Wang et al., "On-Chip Integration of Acceleration, Pressure, and Temperature Composite Sensor with a Single-Sided Micromachining Technique," Journal of Microelctromechanical Systems, vol. 20, No. 1, pp. 42-52, Feb. 2011.

Zhang et al., "Fabrication of Thick Silicon Dioxide Layers Using DRIE, Oxidation and Trench Refill," IEEE, pp. 160-163, 2002.

* cited by examiner

HUMIDITY SENSOR

TECHNICAL FIELD

The disclosure relates generally to humidity sensors and methods for making humidity sensors.

BACKGROUND

Sensors are commonly used to sense one or more properties of a fluid. For example, humidity sensors are often used to measure the relative humidity of a volume or flow of air or other gas. Some humidity sensors, such as capacitive and resistive type humidity sensors, rely on the ability of a sensing material to quickly absorb and desorb water. The absorbed water may alter measurable properties of the sensing material. Heaters may be used to more quickly desorb water between measurements. A need exists for improved humidity sensors that can provide fast and accurate humidity measurements with minimal to no hysteresis while reducing power consumption of the humidity sensor.

SUMMARY

This disclosure relates generally to humidity sensors and methods for making humidity sensors. In one example, a humidity sensor may include a first substrate having a recess formed in a first side, a second substrate and an insulating layer supported by the second substrate. The second substrate and the insulating layer may be supported by the first side of the first substrate and extend over the recess to form a diaphragm with the insulating layer facing the recess. A trench in the second substrate extends around or substantially around the diaphragm and is at least partially filled with a thermally insulating material such as an oxide to help thermally isolate the diaphragm from a remainder of the second substrate. A resistive heater element may be supported by the diaphragm. A pair of sensing electrodes may be electrically separated from each other and supported by the diaphragm. A sensing material may be disposed over the pair of sensing electrodes, wherein an electrical property of the sensing material changes in response to a change in moisture content of the sensing material. The change in the electrical property of the sensing material can be sensed via the pair of sensing electrodes.

In another example, a humidity sensor may include a first silicon substrate having a recess formed in a first side, a second silicon substrate, and an insulating layer that is supported by the second substrate. The second silicon substrate and the insulating layer may be supported by the first side of the first silicon substrate and may extend over the recess of the first silicon substrate to form a diaphragm, with the insulating layer facing the recess. A trench in the second substrate may extend around or substantially around the diaphragm. A resistive heater element may be supported by the diaphragm, and a sensor electrode may be supported by the diaphragm. A sensing layer may be disposed over the sensor electrode, wherein an electrical property of the sensing layer changes in response to changes in moisture content of the sensing layer. The change in the electrical property of the sensing layer may be sensed using the sensor electrode.

In yet another example, a humidity sensor may include a substrate having a hole extending from a first side of the substrate to an opposing second side. An insulating layer may be supported by the first side of the substrate and may extend over the hole in the substrate to form a diaphragm. A resistive heater element may be supported by the diaphragm. In some cases, a pair of sensor electrodes may be electrically separated from each other and may be supported by the diaphragm. A sensing material may be disposed over the pair of sensing electrodes, wherein an electrical property of the sensing material changes in response to a change in moisture content of the sensing material. The change in the electrical property of the sensing material may be sensed via the pair of sensing electrodes.

The preceding summary is provided to facilitate an understanding of some of the features of the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following description of various illustrative embodiments of the disclosure in connection with the accompanying drawings, in which.

Figure 1:
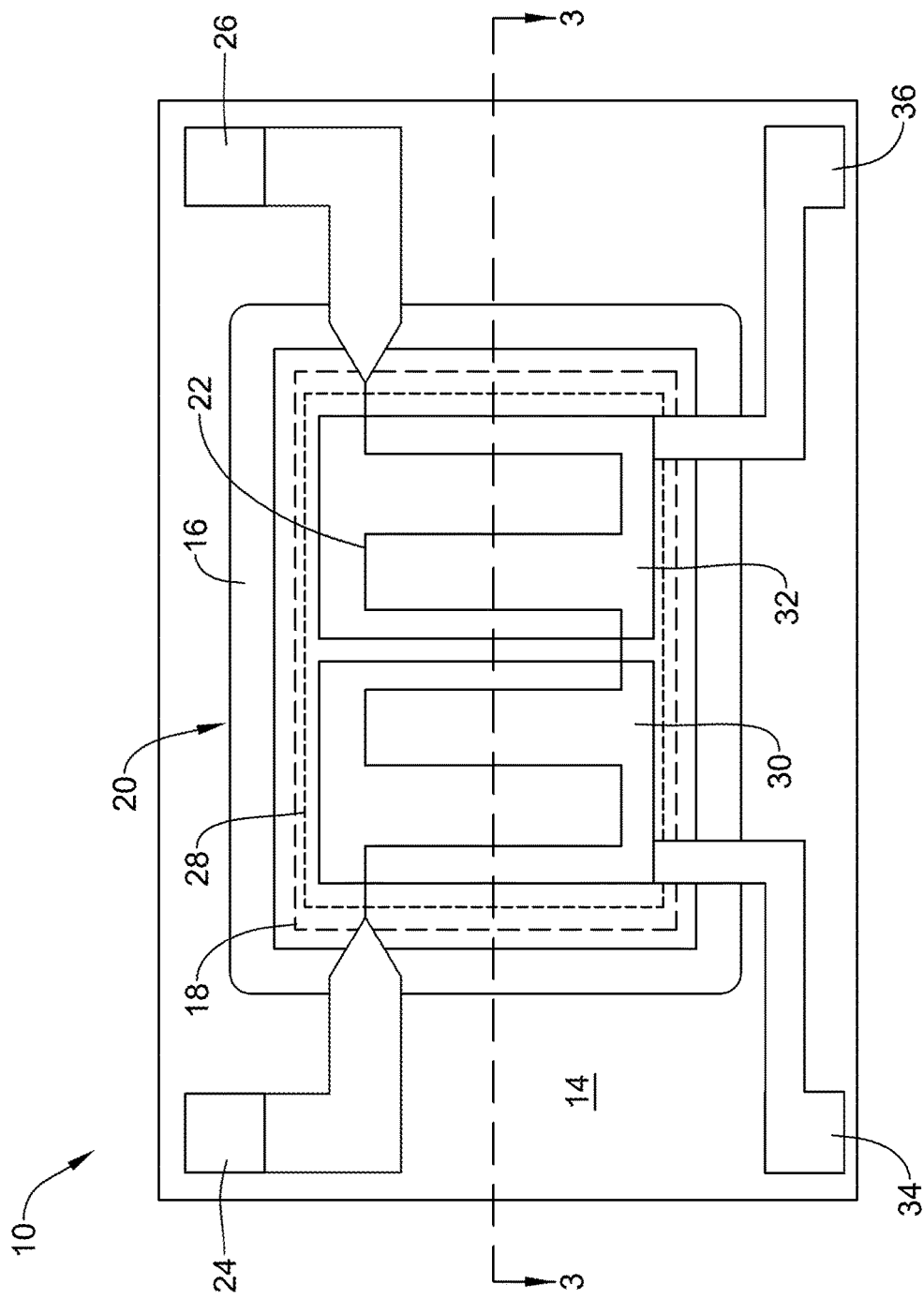
FIG. 1 is a schematic top view of an illustrative humidity sensor.

While the disclosure is amenable to various modifications and alternative forms, specifics thereof have been shown by way of example in the drawings and will be described in detail. It should be understood, however, that the intention is not to limit the disclosure to the particular illustrative embodiments described herein. On the contrary, the intention is to cover all modifications, equivalents, and alternatives falling within the spirit and scope of the disclosure.

DESCRIPTION

The following description should be read with reference to the drawings wherein like reference numerals indicate like elements throughout the several views. References to "over," "under," "top," and "bottom," etc., are relative terms and are made herein with respect to the drawings and do not necessarily correspond to any particular orientation in actual physical space. The description and drawings show several examples that are meant to be illustrative of the claimed disclosure.

Figure 2:
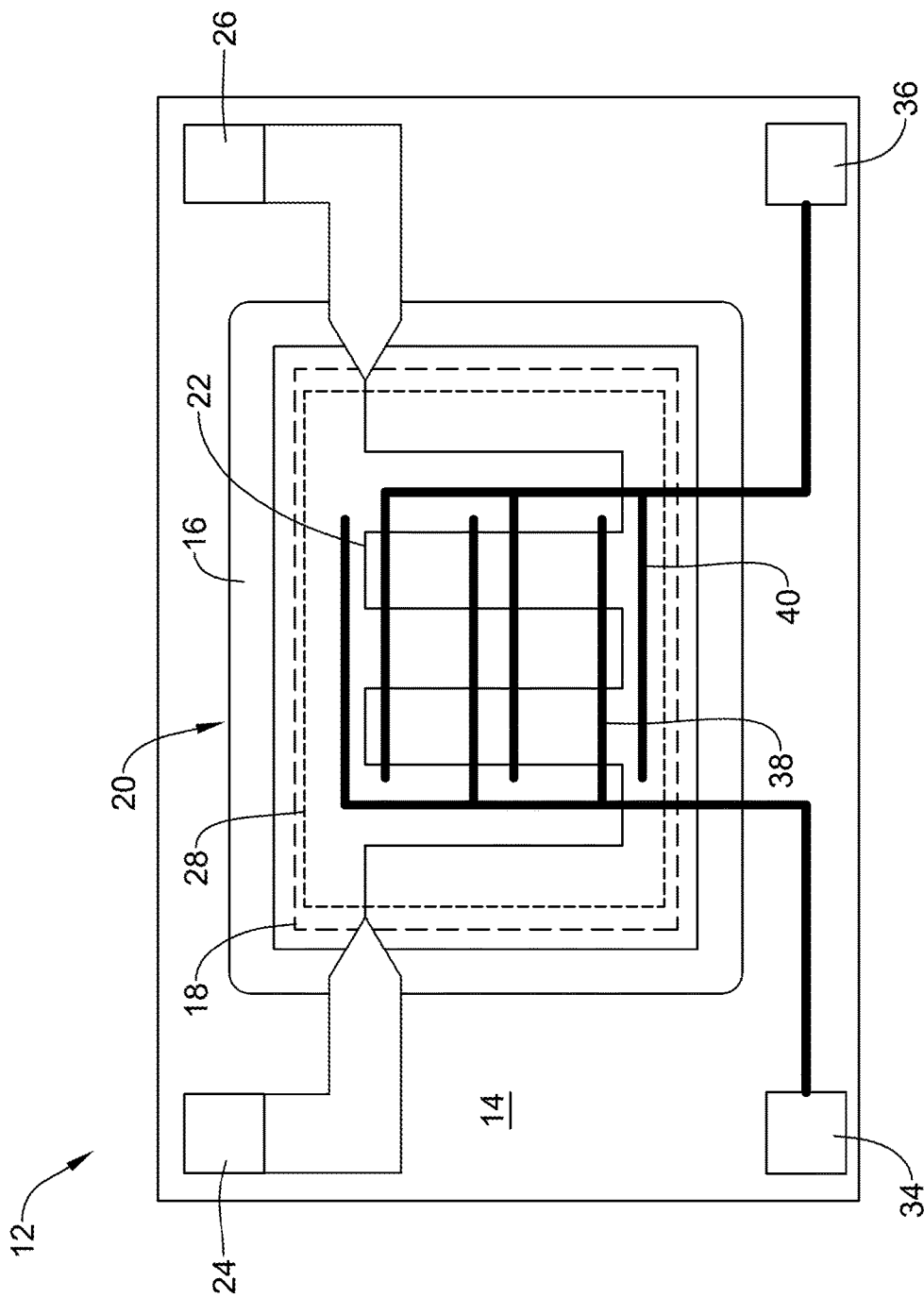
FIG. 2 is a schematic top view of an illustrative humidity sensor similar to that of FIG. 1.

FIG. 1 is a schematic top view of an illustrative sensor assembly 10 and FIG. 2 is a schematic top view of another illustrative sensor assembly 12 that is similar to the sensor assembly 10 but includes a different electrode configuration.

Figure 3:
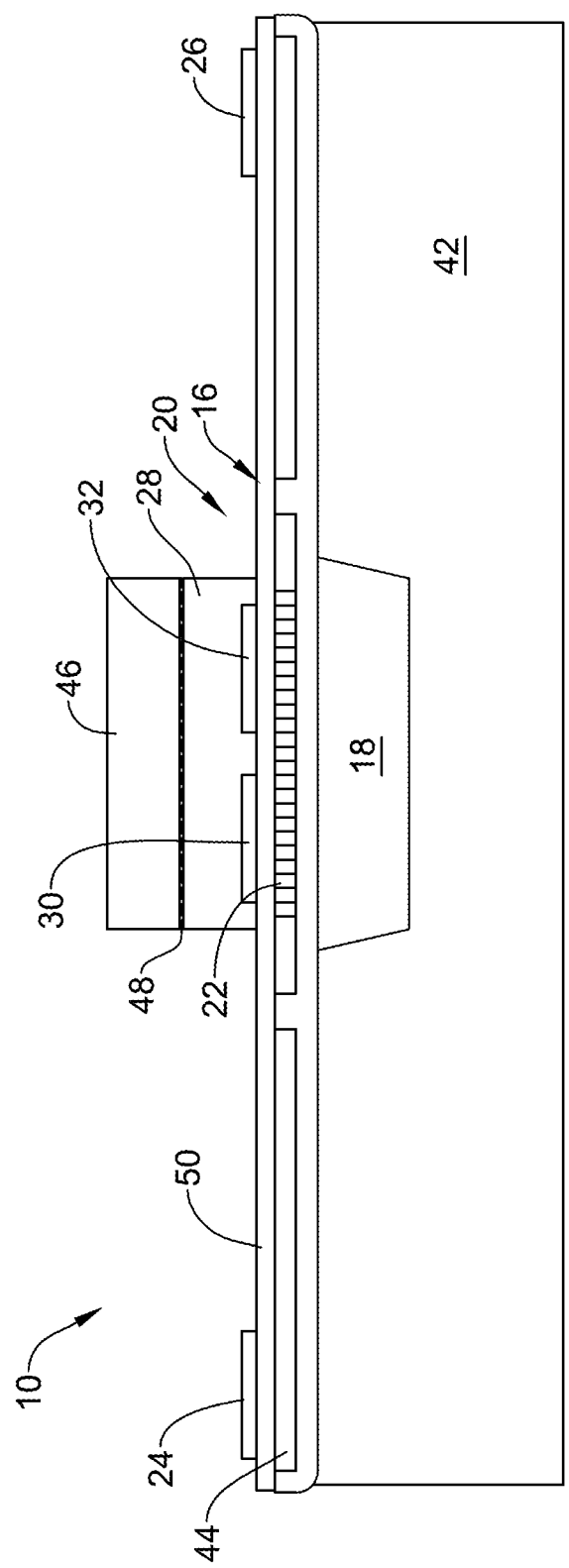
FIG. 3 is a cross-sectional view of the humidity sensor of FIGS. 1 and 2.

FIG. 3 is a cross-sectional view taken along line 3-3 of FIG. 1. It will be appreciated that, depending on exactly where the section line is drawn relative to the electrodes shown in FIG. 2, the sensor assembly 12 may have an identical cross-section.

As illustrated in FIG. 1, the sensor assembly 10 includes an upper surface 14. In the example shown, the upper surface 14 includes a trench 16 which, in some embodiments, may be configured to help thermally isolate portions of the upper surface 14. In some embodiments, as will be illustrated in subsequent drawings, the sensor assembly 10 may include a recess 18 formed under the upper surface 14. In FIG. 1, the recess is denoted by a dashed line labeled 18. It will be appreciated that the portion of the upper surface 14 spanning the recess 18 may be considered as forming a diaphragm 20. The word "diaphragm" may be considered any relatively thin membrane or bridge that extends across the recess 18. In the sensor assembly 10, the diaphragm 20 may help thermally isolate portions of the sensor from the rest of the structure.

In some embodiments, the trench 16 may extend around or substantially around the diaphragm 20. As used herein, the term "substantially around" may mean more than 70% around, more than 80% around, more than 90% around, more than 95% around or more. In some instances, the trench 16 may be formed to circumscribe or substantially circumscribe one or more features supported on the diaphragm 20. Alternatively, or in addition, the trench 16 may be formed to circumscribe or substantially circumscribe a perimeter of the diaphragm 20. In some embodiments, the trench 16 may be filled with a thermally and/or electrically insulating material, such as an oxide (e.g. silicon dioxide) or a nitride (e.g. silicon nitride). A resistive heater element 22 may span across the diaphragm 20, and extends beyond the diaphragm 20 to a first wire bond pad 24 and a second wire bond pad 26. A sensing material is shown disposed over the diaphragm 20 and is denoted by a dashed line 28. It will be appreciated that each of these components are identically illustrated in FIG. 2 as being part of sensor assembly 12.

Returning to FIG. 1, the sensor assembly 10 may include a first sensing electrode plate 30 that is situated laterally adjacent to a second sensing electrode plate 32. In the example shown, the first sensing electrode plate 30 is electrically coupled to a third wire bond pad 34 while the second sensing electrode plate 32 is shown electrically coupled to a fourth wire bond pad 36. In some embodiments, the first sensing electrode plate 30 and/or the second sensing electrode plate 32 may be formed of materials such as silicon, gold, TiW, aluminum, aluminum-copper, copper and silver. In some embodiments, the first sensing electrode plate 30 and/or the second sensing electrode plate 32 may be formed of TiW, gold or silicon.

In some embodiments, the first sensing electrode plate 30 and/or the second sensing electrode plate 32 may be part of a capacitance sensor for measuring the capacitance between the first sensing electrode plate 30 and the second sensing electrode plate 32. The capacitance may change depending on the moisture content in the sensing material, which may depend on the humidity of the air that the sensing material is exposed. In some embodiments, the first sensing electrode plate 30 and/or the second sensing electrode plate 32 may be part of a resistance sensor for measuring the resistance between the first sensing electrode plate 30 and the second sensing electrode plate 32. The resistance may change depending on the moisture content in the sensing material, which may depend on the humidity of the air that the sensing material is exposed.

In FIG. 2, the sensor assembly 12 may include a first sensing electrode 38 and a second sensing electrode 40 that is interdigitated with the first sensing electrode 38. The first sensing electrode 38 is shown electrically coupled to a third wire bond pad 34 and the second sensing electrode 40 is electrically coupled to a fourth wire bond pad 36. In some embodiments, the first sensing electrode 38 and/or the second sensing electrode 40 may be formed of materials such as silicon, gold, TiW, aluminum, aluminum-copper, copper and silver. In some embodiments, the first sensing electrode 38 and/or the second sensing electrode 40 may be formed of TiW, gold or silicon.

In some embodiments, the first sensing electrode 38 and/or the second sensing electrode 40 may be part of a capacitance sensor for measuring the capacitance between the first sensing electrode 38 and the second sensing electrode 40. The capacitance may change depending on the moisture content in the sensing material, which may depend on the humidity of the air that the sensing material is exposed. In some embodiments, the first sensing electrode 38 and/or the second sensing electrode 40 may be part of a resistance sensor for measuring the resistance between the first sensing electrode 38 and the second sensing electrode 40. The resistance may change depending on the moisture content in the sensing material, which may depend on the humidity of the air that the sensing material is exposed.

FIG. 3 provides additional details regarding the structure of the sensor assembly 10. As will be illustrated in subsequent drawings, the sensor assembly 10 may be formed from a first substrate 42 and a second substrate 44. In some embodiments, the sensor assembly 10 includes a protective polyimide cap or cap layer 46 that is disposed over the sensing material 28. In some embodiments, a porous metal layer 48 is deposited between the sensing material 28 and the cap layer 46. If present, the porous metal layer 48 may include platinum or gold. In some cases, a dielectric layer 50 (or other layer) may span across the sensor assembly 10. The sensor assembly 10 may be constructed in a variety of different ways. In some embodiments, as illustrated, the trench 16 is formed in the second substrate 44, and does not overlap (in a vertical direction in FIG. 3) the recess 18 formed in the first substrate 42. FIGS. 4 through 10 provide schematic illustrations of an example construction method for sensor assembly 10.

Figure 4:
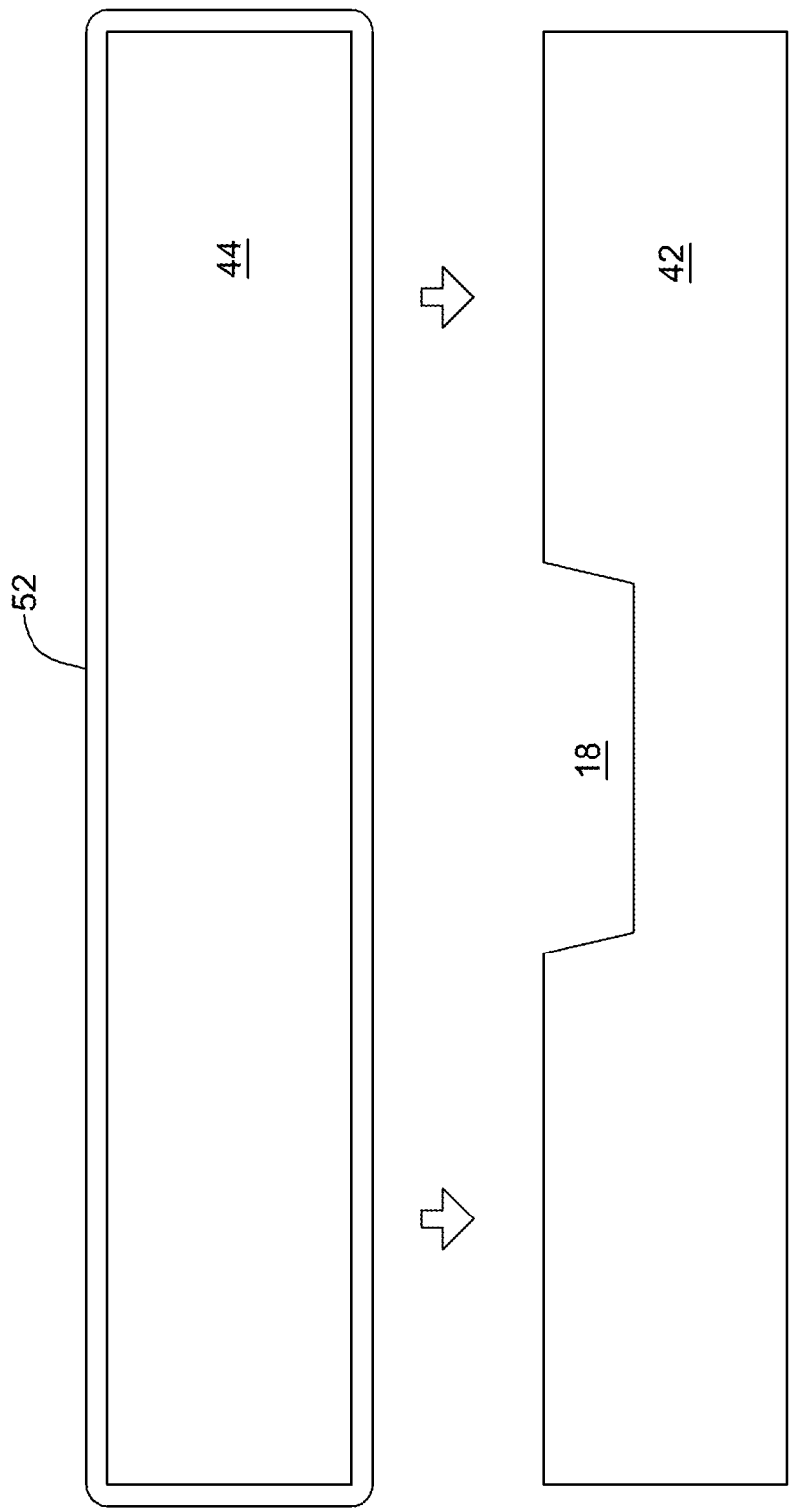
FIGS. 4-10 illustrate schematic cross-sectional views of an illustrative process for forming the humidity sensor of FIGS. 1 and 2.

As shown in FIG. 4, formation of the sensor assembly 10 may begin by positioning the second substrate 44 over the first substrate 42. The first substrate 42 may be formed of any suitable material, and may be formed in any suitable manner. In some embodiments, suitable materials for forming the first substrate 42 may include silicon, silicon oxide, silicon nitride, titanium oxide, aluminum oxide, silicon carbide, gallium arsenide, ceramic, metal, and/or any other suitable material or material combinations, as desired. In some embodiments, the second substrate 44 may be a semiconductor such as silicon. The material used to form the first substrate 42 may, for example, be selected such that the first substrate 42 has a similar coefficient of thermal expansion (CTE) to that of the second substrate 44.

Figure 5:
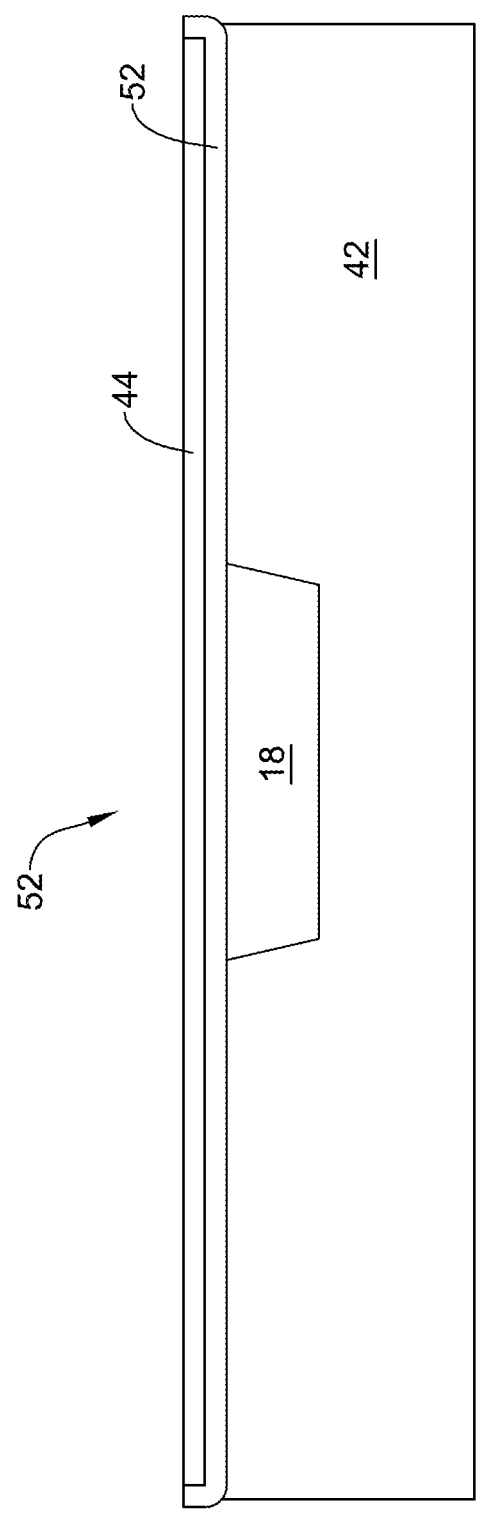

In some embodiments, as illustrated, the first substrate 42 already includes the recess 18. In some embodiments, as shown, the second substrate 44 includes an oxide layer 52 on the outer surface. The second substrate 44 may be bonded to the first substrate 42 using any suitable bonding technique, including but not limited to frit bonding, anodic bonding, fusion bonding, adhesion bonding, eutectic bonding, soldering, welding, metal diffusion or UV. The first substrate 42 and/or the second substrate 44 may, if desired, include or otherwise be formed of silicon. In some cases, after the second substrate 44 is bonded to the first substrate 42, the second substrate 44 may be polished or etched to provide a desired thickness for the diaphragm 20. The resulting assembly is shown in FIG. 5.

Figure 6:
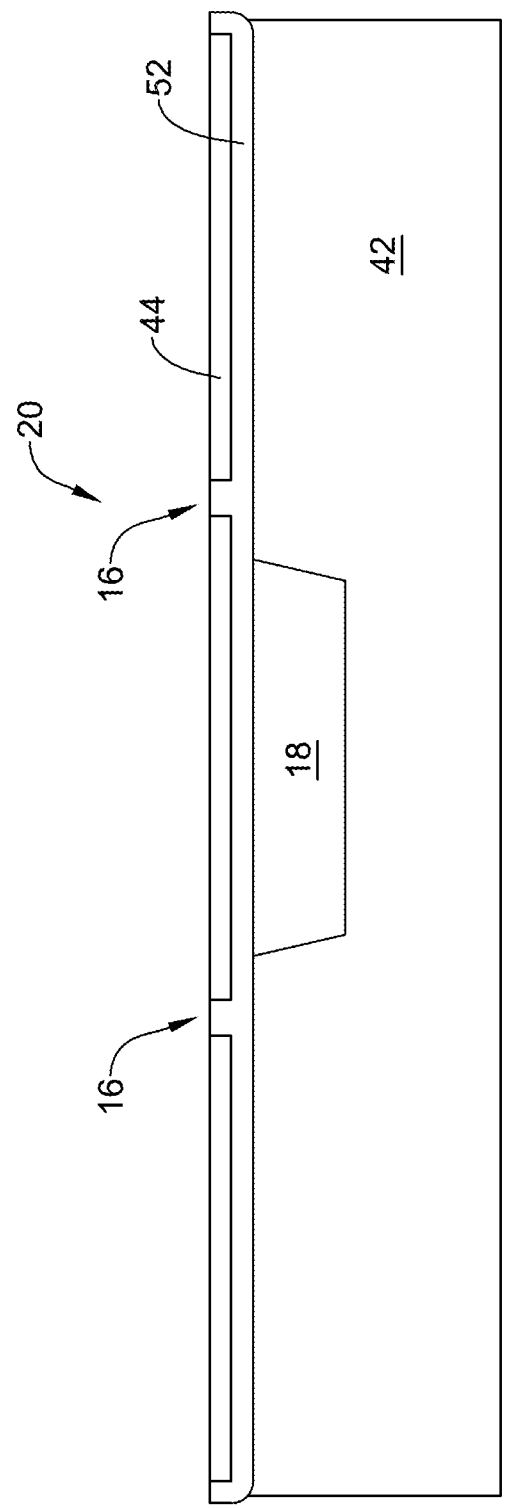

Turning now to FIG. 6, it can be seen that the assembly has been further processed to form the trench 16. In forming the trench 16, the second substrate 44 is further etched or otherwise processed to remove sufficient silicon to form a shape that extends around or substantially around the diaphragm 20. The shape may then be filled with silicon oxide or other suitable material to complete the trench 16, as shown in FIG. 6. It will be appreciated that the trench 16 may help to thermally and/or electrically isolate the diaphragm 20 from the rest of the structure, such as from first substrate 42 and the rest of second substrate 44.

Figure 7:
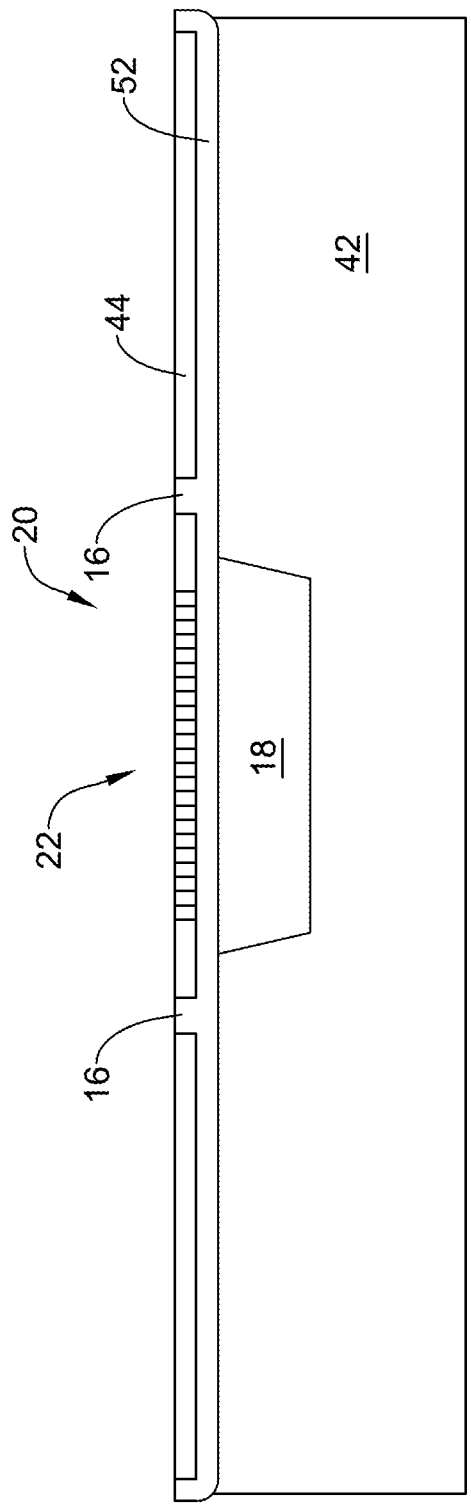
Figure 8:
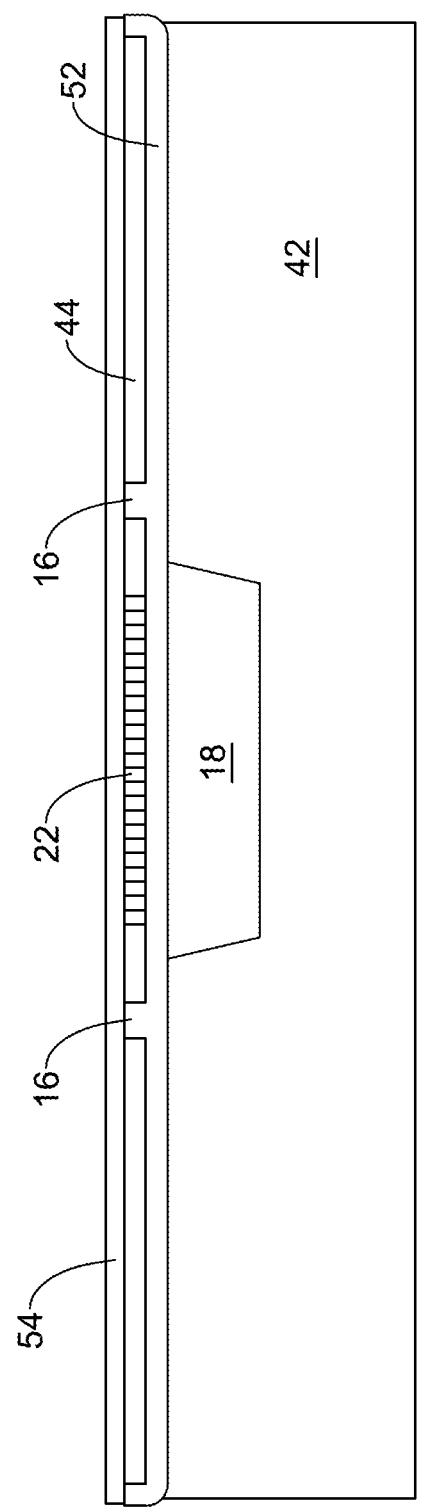

Turning to FIG. 7, it can be seen that the resistive heater element 22 may be formed by providing resistors within or on the second substrate 44 and on the diaphragm 20. In some embodiments, the resistive heater element 22 may be formed via ion implantation or diffusion. In some cases, the resistors may be silicide (Pt, Au, Pd, Mo, Ti, W, Hf, Zr, Cr, or combinations thereof) resistors, but this is not required. The resistive heater element 22 may be formed of materials such as silicon, Permalloy, and nichrome. In some embodiments, the resistive heater element 22 may be formed of silicon, Permalloy or platinum. In some cases, the resistive heating element may be provided along a meandering path to extend the effective length of the resistive heater element 22. In some embodiments, the sensor assembly 10 may include other resistors for other purposes (not illustrated), and these resistors, if present, may also be formed at this time. A dielectric layer 54 or other layer may be provided over the resistive heater element 22, as shown for example in FIG. 8. The dielectric layer 54 may be formed of any suitable material, such as silicon dioxide or silicon nitride.

Figure 9:
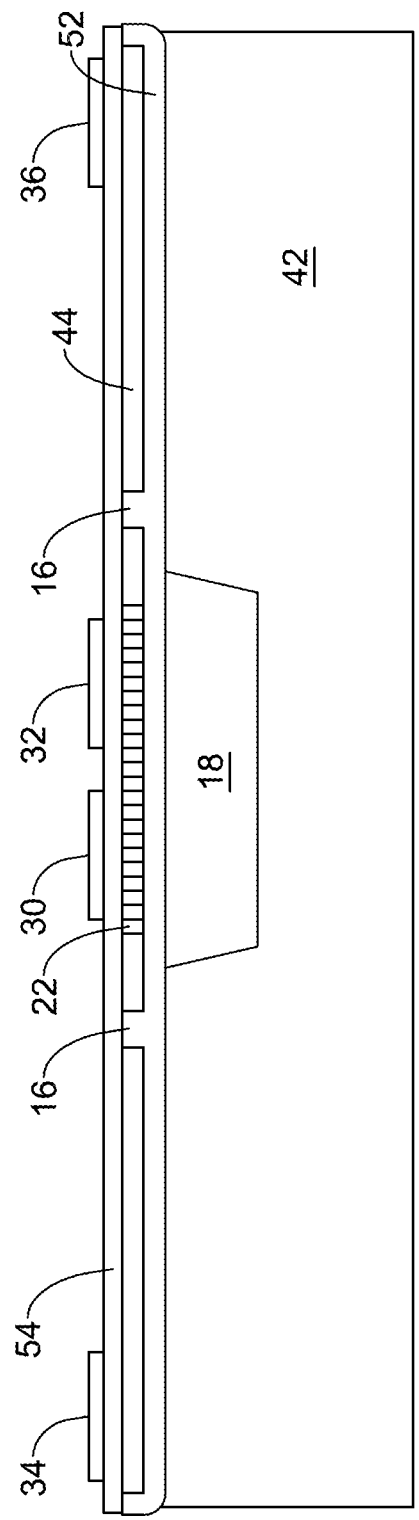

As illustrated in FIG. 9, a metal layer may be deposited and patterned to form elements such as the first sensing electrode plate 30 and the second sensing electrode plate 32, and wire bond pads such as the third wire bond pad 34 and the fourth wire bond pad 36. Electrical contacts for other components may also be formed at this time, including, for example, the first wire bond pad 24 and the second wire bond pad 26 that provide an electrical connection to the resistive heater element 22.

Figure 10:
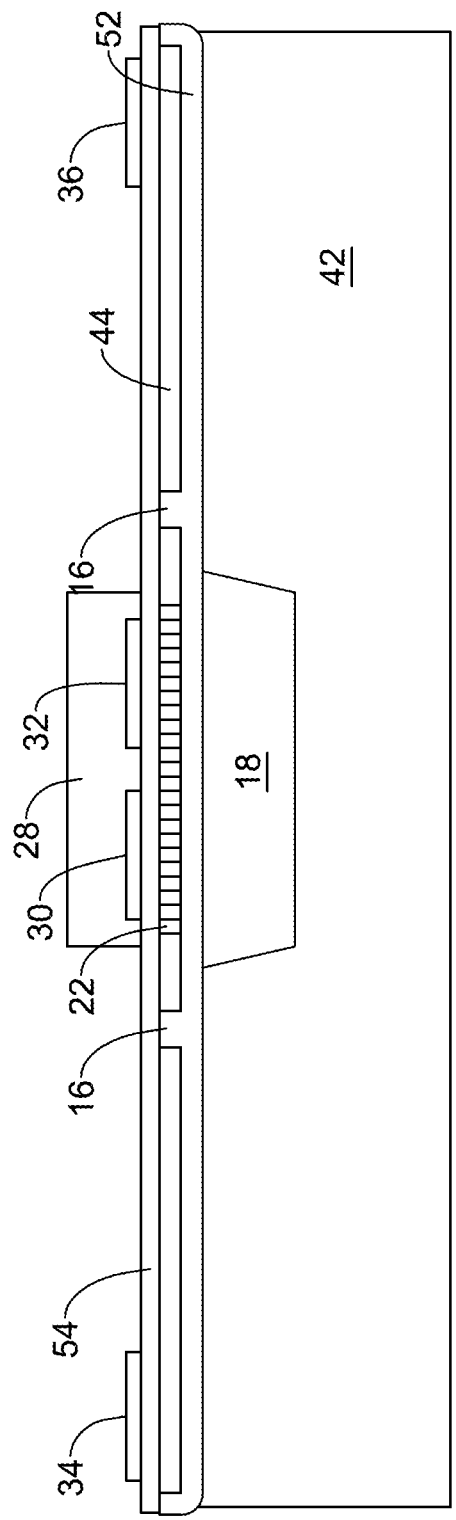

Turning now to FIG. 10, the sensing material 28 may be deposited or otherwise provided over the first sensing electrode plate 30 and the second sensing electrode plate 32. The sensing material 28 may include any suitable material, such as a polyimide, that has an electrical property that changes in response to changes in the moisture content of the sensing material 28. In some embodiments, the sensing material 28 may include one or more of benzocyclobutene (BCB), commercially available from Dow as CYLCOTENE, PMMA, polypyrrole, and fluoropolymers such as HQDEA/4-BDAF and fluorovinylethers, and the like. Accordingly, the first sensing electrode plate 30 and the second sensing electrode plate 32 (or the interdigitated first sensing electrode 38 and second sensing electrode 40 as shown in FIG. 2) may be positioned to pick up a change in resistance, capacitance or other suitable electrical property. In some embodiments, as shown in FIG. 3, the porous metal layer 48 and/or the cap layer 46 may optionally be formed above the sensing material 28.

Figure 11:
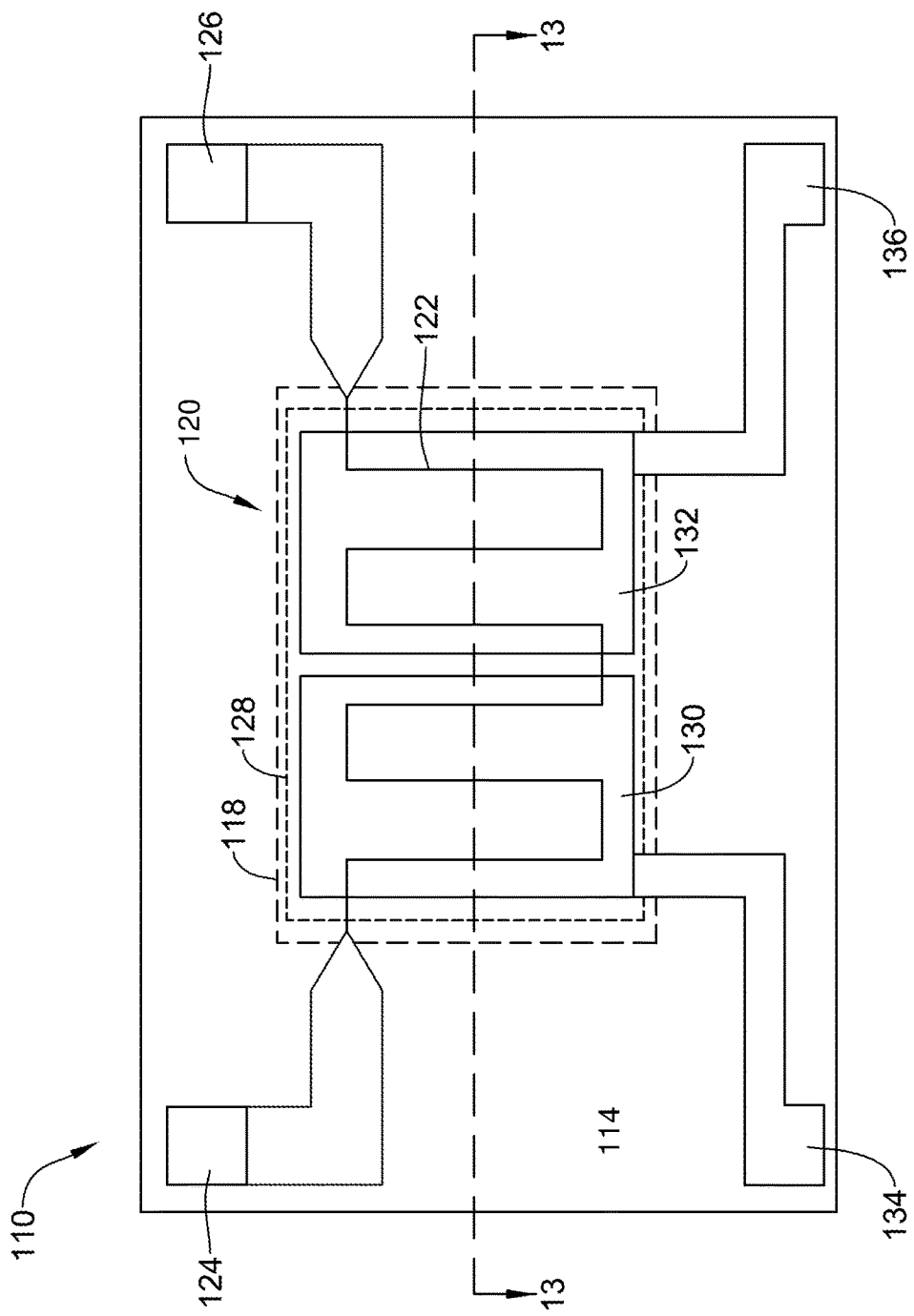
FIG. 11 is a schematic top view of another illustrative humidity sensor.
Figure 12:
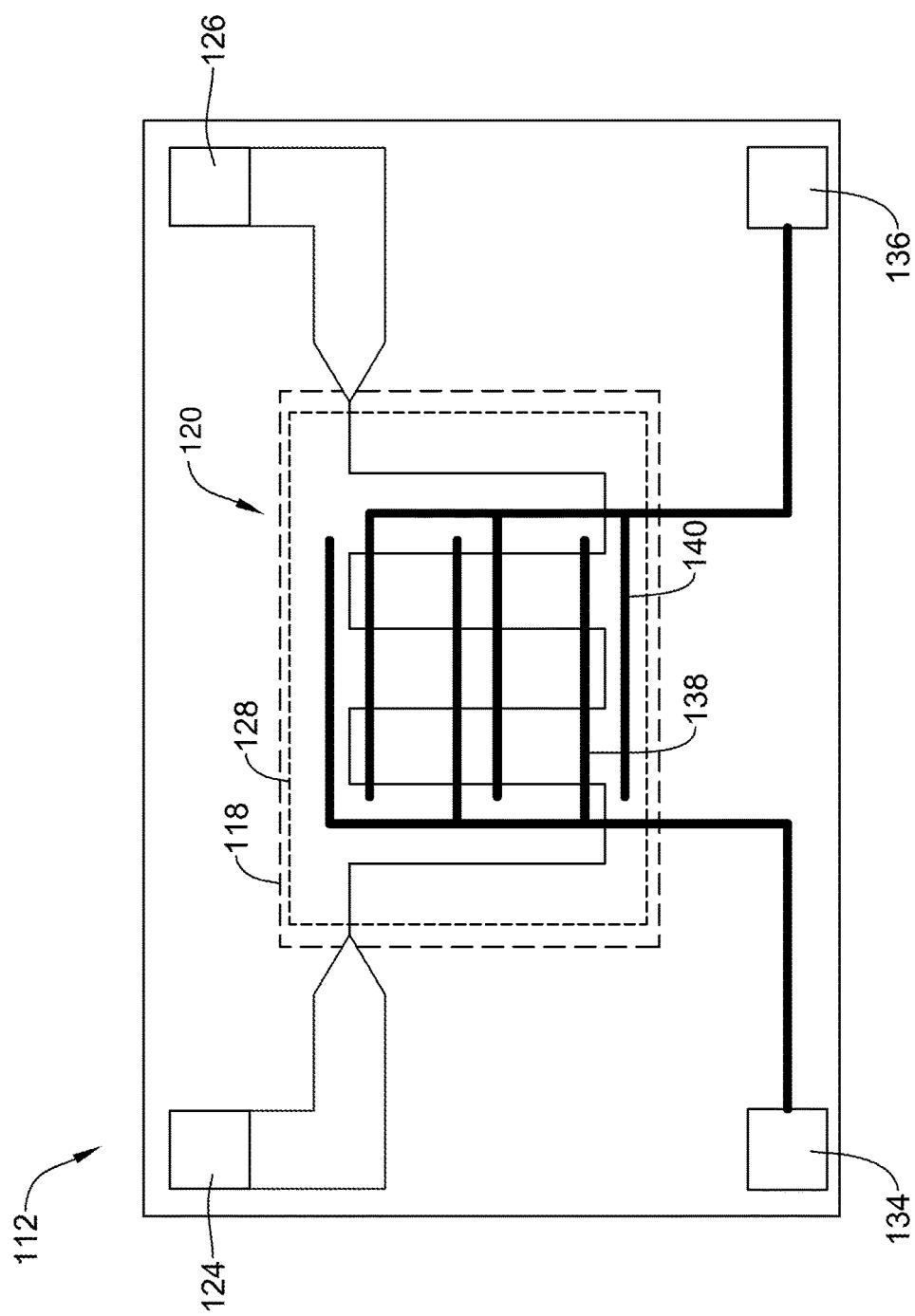
FIG. 12 is a schematic top view of an illustrative humidity sensor similar to that of FIG. 11.
Figure 13:
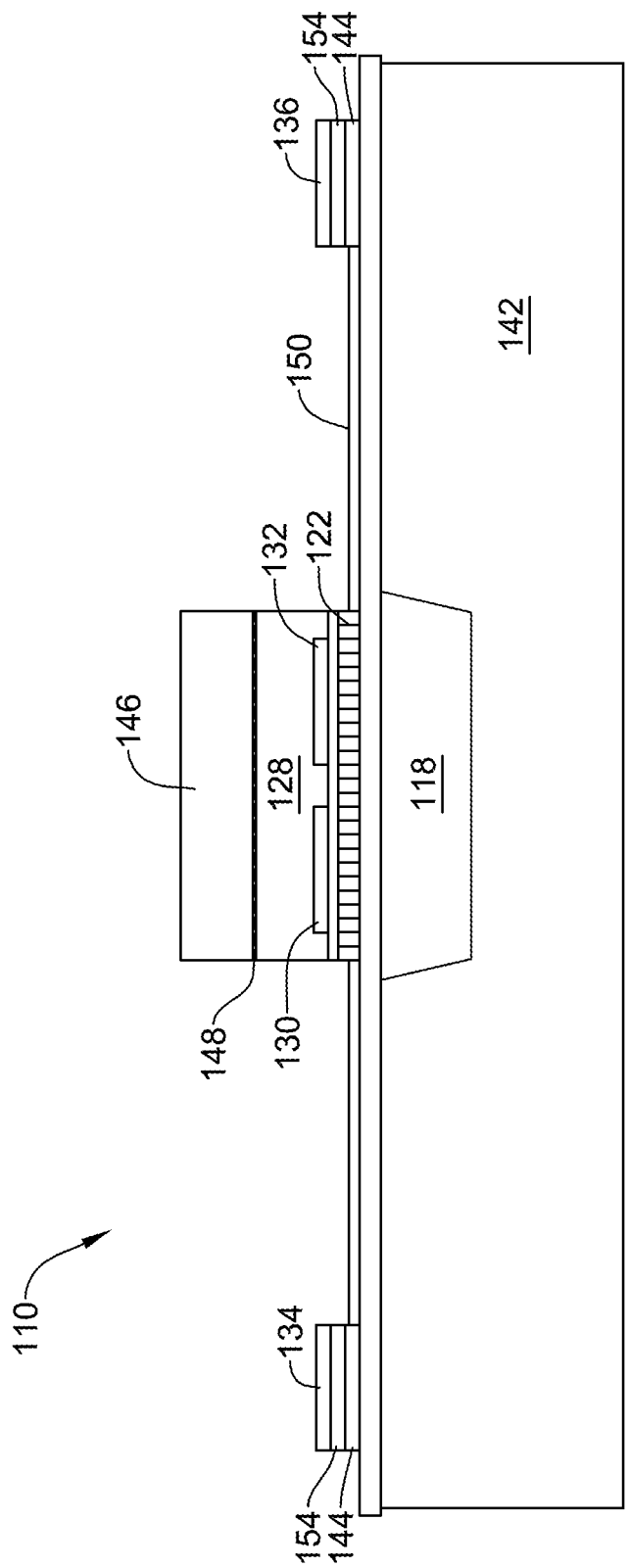
FIG. 13 is a cross-sectional view of the humidity sensor of FIGS. 11 and 12.

FIG. 11 is a schematic top view of another illustrative sensor assembly 110 and FIG. 12 is a schematic top view of an illustrative sensor assembly 112 that is similar to the illustrative sensor assembly 110 but includes a different electrode configuration. FIG. 13 is a cross-sectional view taken along line 13-13 of FIG. 11. It will be appreciated that, depending on exactly where the section line is drawn relative to the electrodes shown in FIG. 12, the sensor assembly 112 may have an identical cross-section.

As illustrated in FIG. 11, the sensor assembly 110 includes an upper surface 114. In some embodiments, as will be illustrated in subsequent drawings, the sensor assembly 110 may include a recess 118 formed under the upper surface 114. In FIG. 11, the recess is denoted by a dashed line 118. It will be appreciated that the portion of the upper surface 114 spanning the recess 118 may be considered as forming a diaphragm 120. A resistive heater element 122 is shown spanning across the diaphragm 120, and extending beyond the diaphragm 120 to a first wire bond pad 124 and a second wire bond pad 126. A sensing material 128 is shown disposed over the diaphragm 120, and is denoted by a dashed line 128. It will be appreciated that each of these components are identically illustrated in FIG. 12 as being part of the sensor assembly 112.

Returning to FIG. 11, the illustrative sensor assembly 110 includes a first sensing electrode plate 130 that is situated laterally adjacent to a second sensing electrode plate 132. The first sensing electrode plate 130 is electrically coupled to a third wire bond pad 134 while the second sensing electrode plate 132 is electrically coupled to a fourth wire bond pad 136. In FIG. 12, by contrast, the sensor assembly 112 includes a first sensing electrode 138 and a second sensing electrode 140 that is interdigitated with the first sensing electrode 138. The first sensing electrode 138 is electrically coupled to the third wire bond pad 134 and the second sensing electrode 140 is electrically coupled to the fourth wire bond pad 136.

FIG. 13 provides additional details regarding the structure of the sensor assembly 110. As will be illustrated in subsequent drawings, the sensor assembly 110 may be formed from a first substrate 142 and a second substrate 144. In some embodiments, the sensor assembly 110 includes a protective polyimide cap or cap layer 146 that is disposed over the sensing material 128. In some embodiments, a porous metal layer 148 is deposited between the sensing material 128 and the cap layer 146. A dielectric layer 150 (or other layer) is shown spanning across the sensor assembly 110. The sensor assembly 110 may be constructed in a variety of different ways. FIGS. 14 through 19 provide schematic illustrations of an example construction method.

Figure 14:
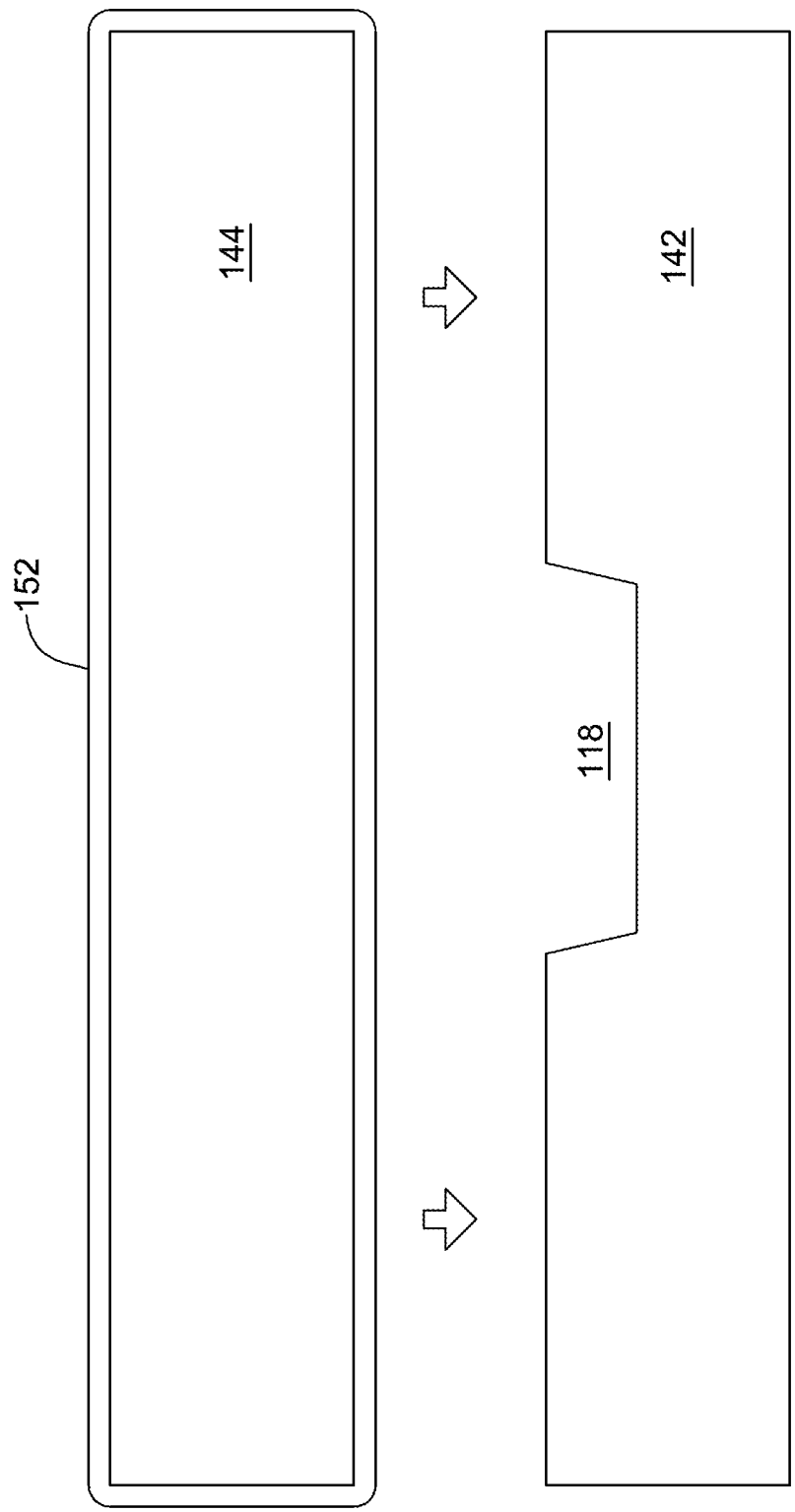
FIGS. 14-19 illustrate schematic cross-sectional views of an illustrative process for forming the humidity sensor of FIGS. 12 and 13.
Figure 15:
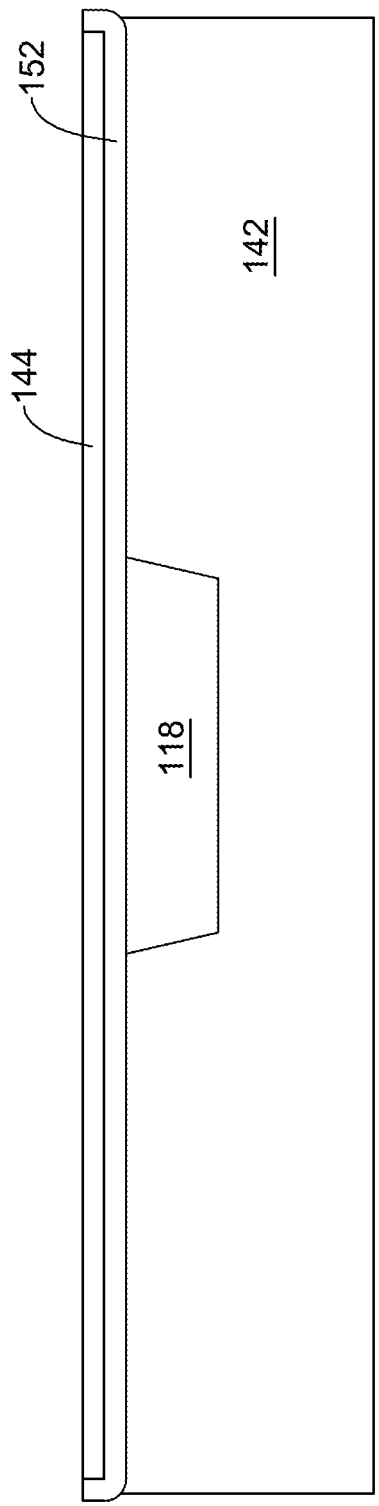

As shown in FIG. 14, formation of the sensor assembly 110 begins by positioning the second substrate 144 over the first substrate 142. In some embodiments, as illustrated, the first substrate 142 already includes the recess 118. In some embodiments, as shown, the second substrate 144 includes an oxide layer 152. The second substrate 144 may be bonded to the first substrate 142 using any suitable technique, including but not limited to frit bonding, anodic bonding, fusion bonding, adhesion bonding, eutectic bonding, soldering, welding, metal diffusion or UV. The first substrate 142 and/or the second substrate 144 may, if desired, include or otherwise be formed of silicon. In some cases, after the second substrate 144 is bonded to the first substrate 142, the second substrate 144 may be polished or etched to provide a desired thickness for the diaphragm 120. The resulting assembly may be seen in FIG. 15. In some cases, the second substrate 144 may be etched away, leaving only the oxide layer 152 to form the diaphragm 120.

Figure 16:
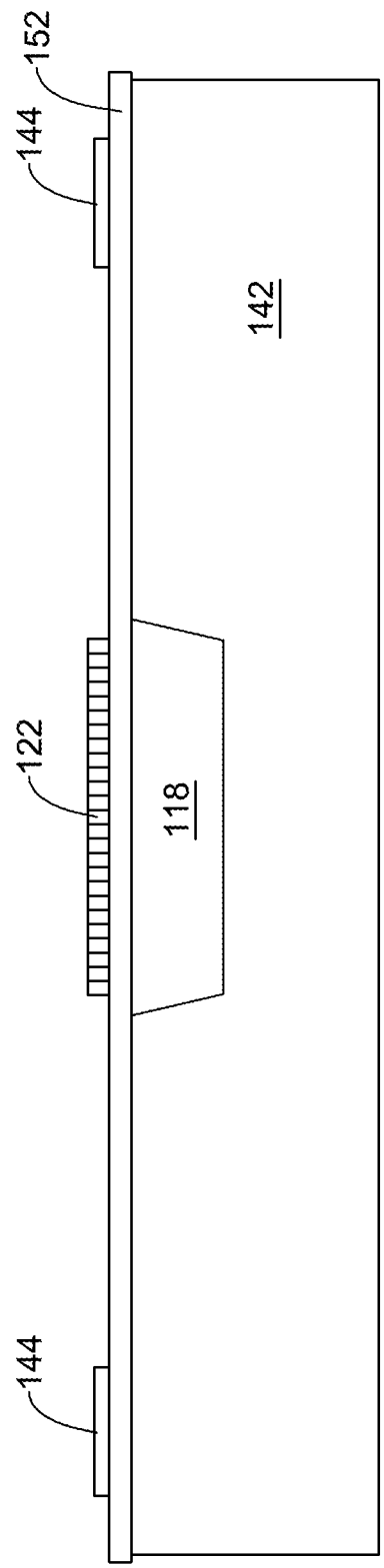

Turning now to FIG. 16, it can be seen that the resistive heating element 122 may be formed by providing resistors within or on the oxide layer 152 and on the diaphragm 120. In some embodiments, the resistive heating element 122 may be formed via ion implantation or diffusion into the second substrate 144 before etching away the adjacent parts of the second substrate 144. In other cases, one or more resistive layers may be formed on the oxide layer 152 after the second substrate 144 is etched away. In some cases, the second substrate 144 may not be etched away in the regions of the first wire bond pad 124 and the second wire bond pad 126 as shown in FIG. 16, but this is not required. The etching of the second substrate 144 between the resistive heating element 122 and the first wire bond pad 124 and/or the second wire bond pad 126 may be considered a trench that extends around or substantially around the diaphragm 120 and overlaps (in a vertical direction in FIG. 16) the recess 118 formed in the first substrate 142. When the resistive heating element 122 is not formed using the second substrate 144, but rather is provided as a separate heating element or layer on oxide layer 152, a trench may be considered to be formed between the first wire bond pad 124 and the second wire bond pad 126, and in some cases, the trench may completely remove the first substrate 142 thereby leaving only the oxide layer 152 even in the regions of the first wire bond pad 124 and the second wire bond pad 126. These are just some examples.

Figure 17:
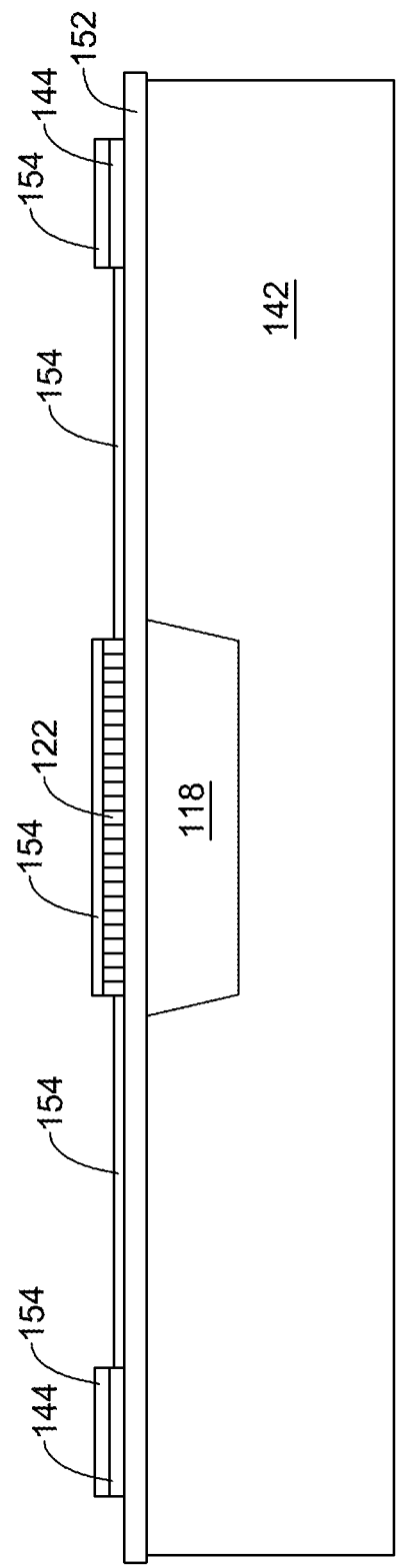

In some cases, a dielectric layer 154 may be deposited over the resistive heating element 122 and the oxide layer 152, as shown for example in FIG. 17. The dielectric layer 154 may be formed of any desired material, although in some embodiments the dielectric layer 154 may include or otherwise be formed from silicon dioxide or silicon nitride. In some cases, the dielectric layer 154 may be patterned to cover the resistive heating element 122 but to not extend laterally past the diaphragm 120 and onto oxide layer 152. When so provided, it may be desirable to form the dielectric layer 154 from a thermally conductive, electrically insulating material that helps conduct heat from the heater element up to the sensing material 128. In some embodiments, the dielectric layer 154 may be formed from silicon oxide and/or silicon nitride, and may be a thin layer having a thickness in the range of about 10 to about 2000 nanometers (nm).

Figure 18:
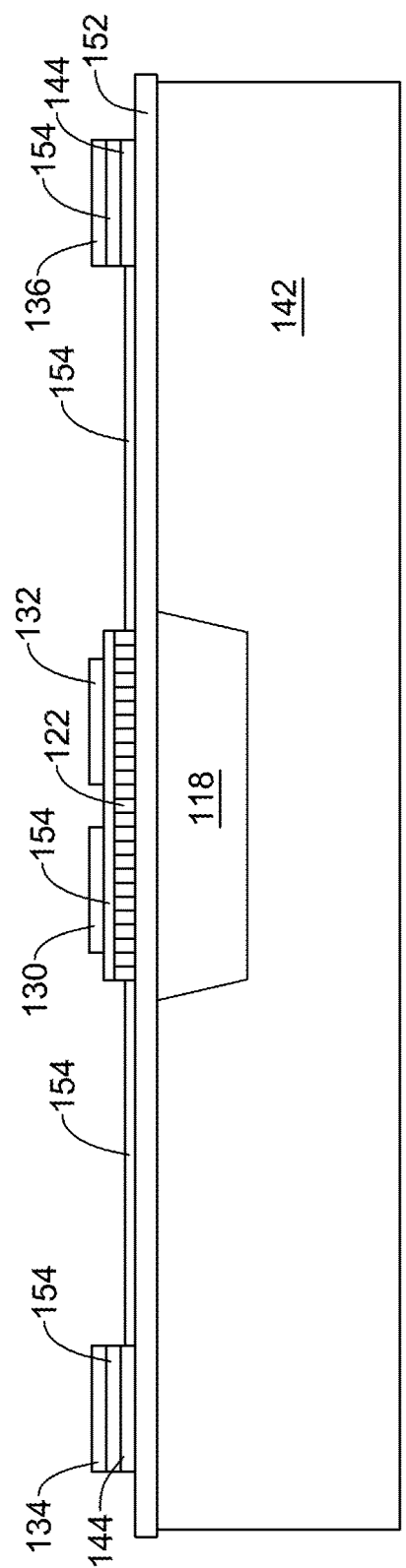

As illustrated in FIG. 18, a metal layer may be deposited and patterned to form elements such as the first sensing electrode plate 130 and the second sensing electrode plate 132, and wire bond pads such as the third wire bond pad 134 and the fourth wire bond pad 136. Electrical contacts for other components may also be formed at this time, including, for example, the first wire bond pad 124 and the second wire bond pad 126 that provide electrical communication with the resistive heater element 122.

Figure 19:
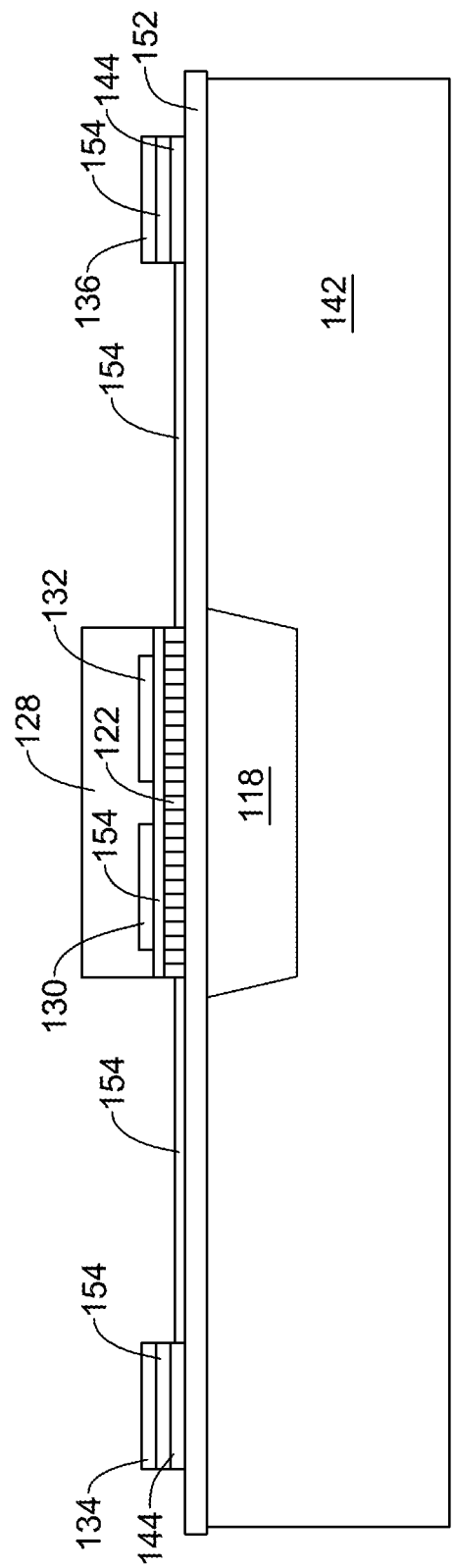

Turning to FIG. 19, the sensing material 128 may be deposited over the first sensing electrode plate 130 and the second sensing electrode plate 132. The sensing material 128 includes a material, such as a polyimide, that has an electrical property that changes in responses to changes in the moisture content of the sensing material 128. In some embodiments, as shown in FIG. 13, the porous metal layer 148 and/or the cap layer 146 may optionally be formed if desired.

Figure 20:
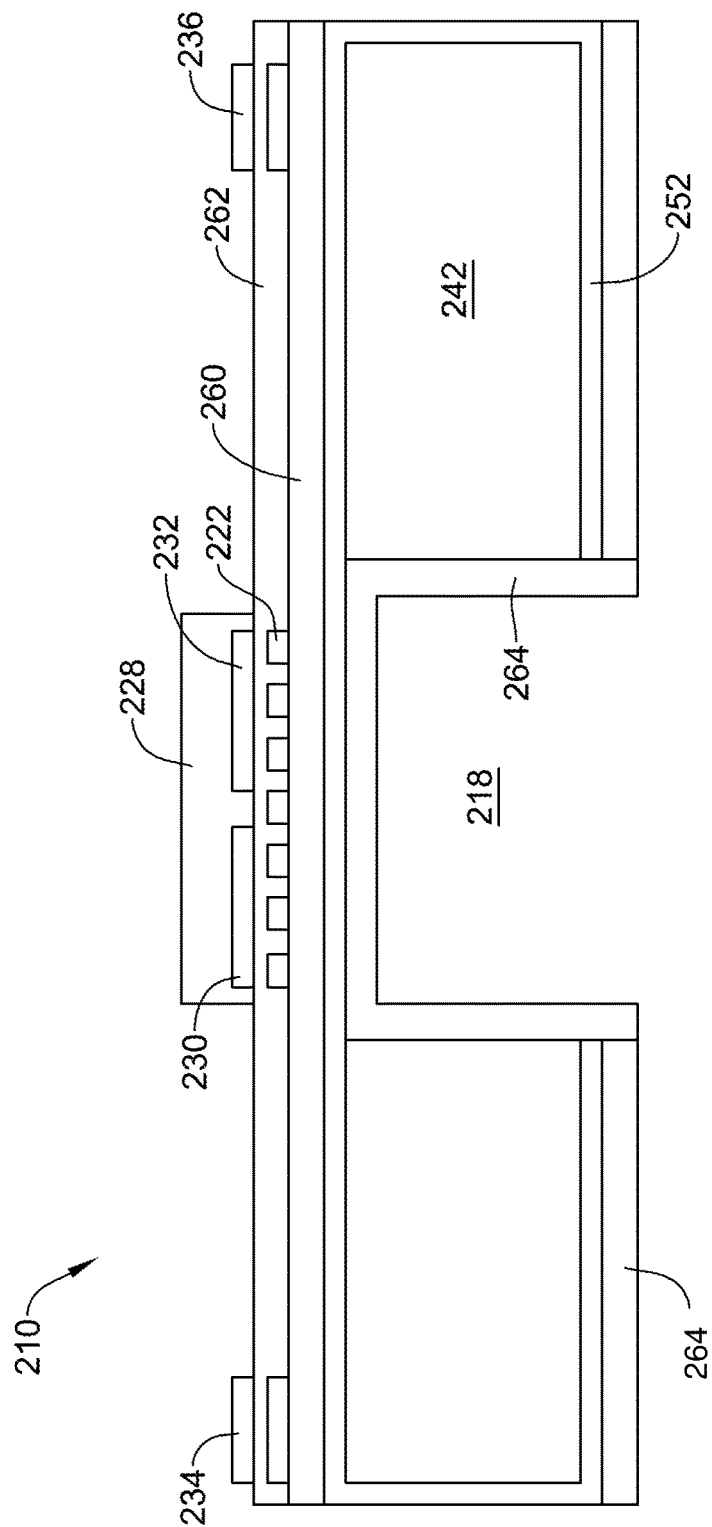
FIG. 20 is a schematic cross-sectional view of yet another illustrative humidity sensor.

FIG. 20 is a schematic cross-sectional view of a sensor assembly 210. In some embodiments, the sensor assembly 210 may be formed from a single substrate 242 such as a silicon wafer. In the example shown, the single substrate 242 includes an oxide layer 252 that essentially covers the substrate 242. Upper and lower surfaces of the substrate 242 may include a silicon nitride layer 260 that may be formed using any suitable technique, such as sputtering or LPCVD (low pressure chemical vapor deposition). A resistive heater element 222 may be disposed on the silicon nitride layer 260. First and second sensing electrodes 230 and 232 are disposed above the resistive heater element 222 and below a sensing material 228. Wire bond pads 234 and 236 are also provided. In some embodiments, an insulating or low thermal conductivity material 264 lines the inner surface of a recess 218 formed within the substrate 242. FIGS. 21 through 27 provide schematic illustrations of an example construction method.

Figure 21:
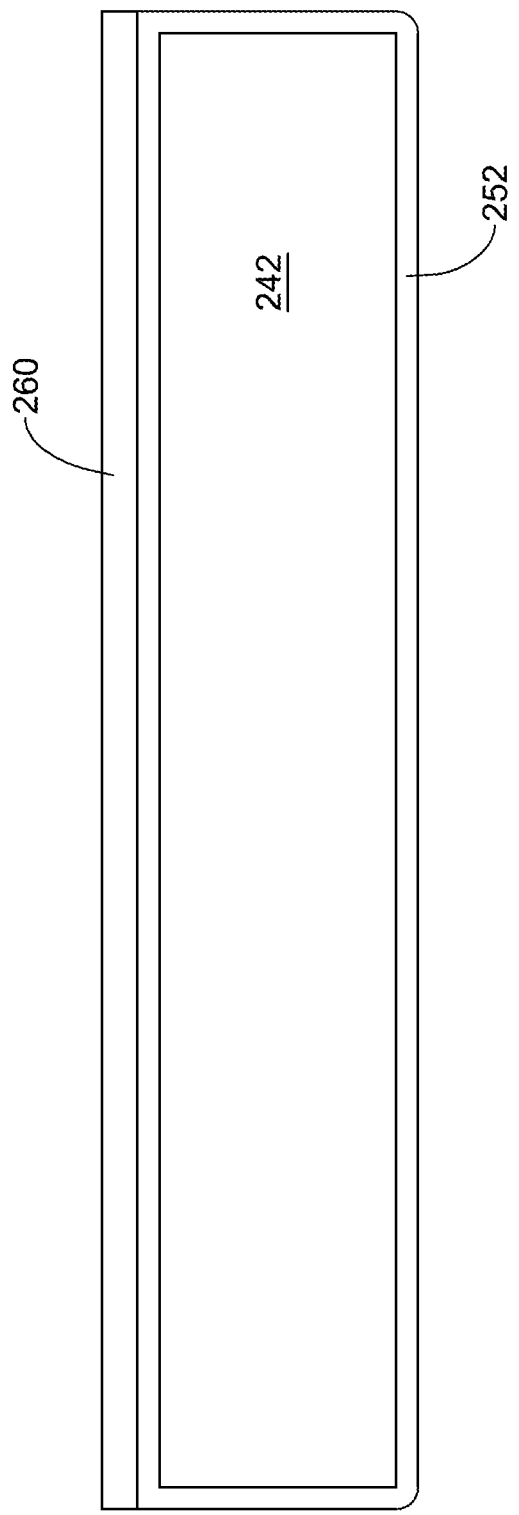
FIGS. 21-27 illustrate schematic cross-sectional views of an illustrative process for forming the humidity sensor of FIG. 20.
Figure 22:
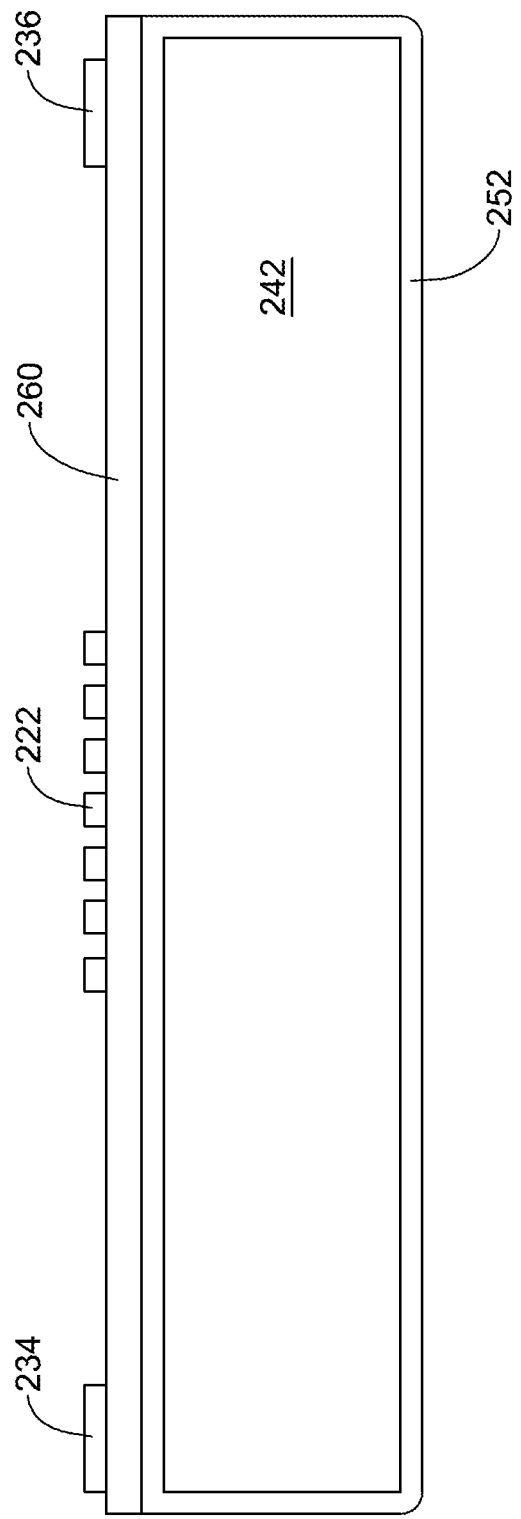

As shown in FIG. 21, a substrate 242 may be oxidized to form an oxidized layer 252. One surface of the oxidized layer 252 may be coated with silicon nitride to form a silicon nitride layer 260. In some embodiments, the silicon nitride layer 260 may be formed using any suitable technique such as sputtering or low pressure chemical vapor deposition. The resistive heater element 222 may be formed by depositing, patterning and etching any suitable resistive layer, as shown in FIG. 22.

Figure 23:
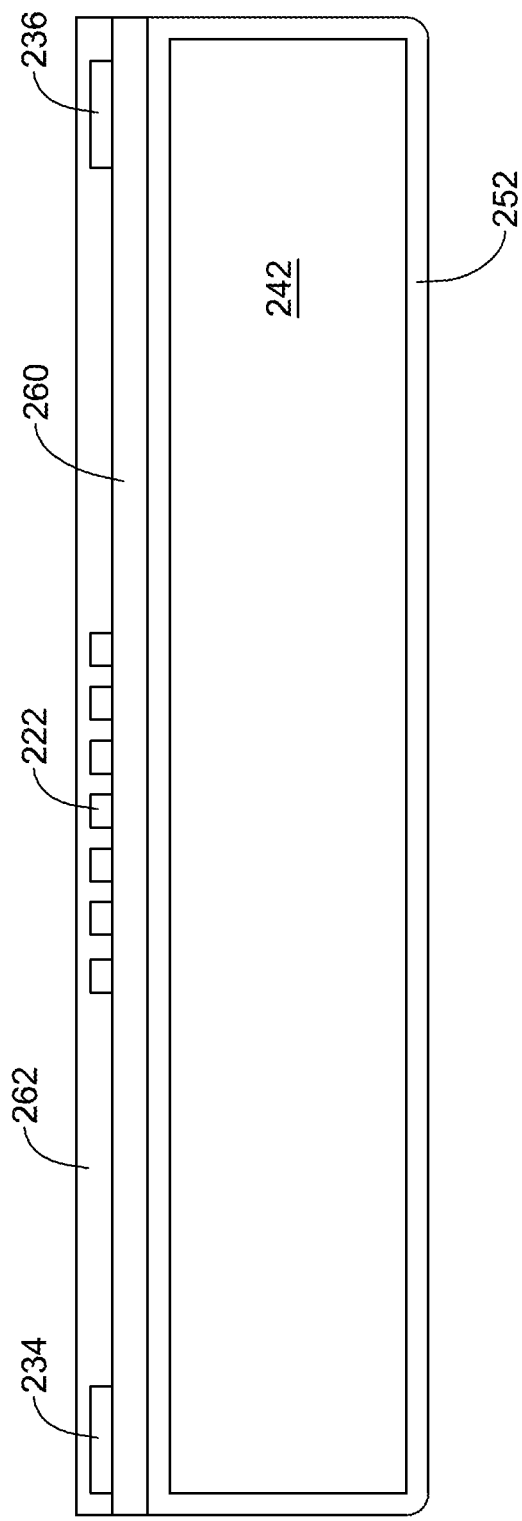
Figure 24:
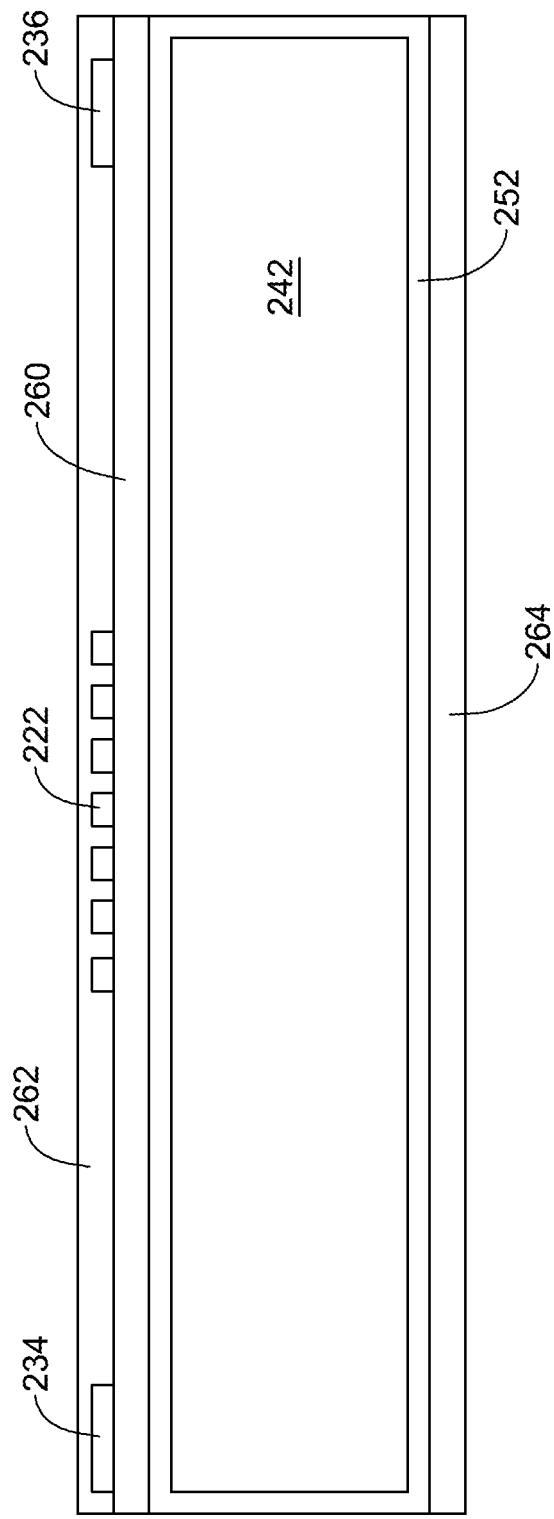
Figure 25:
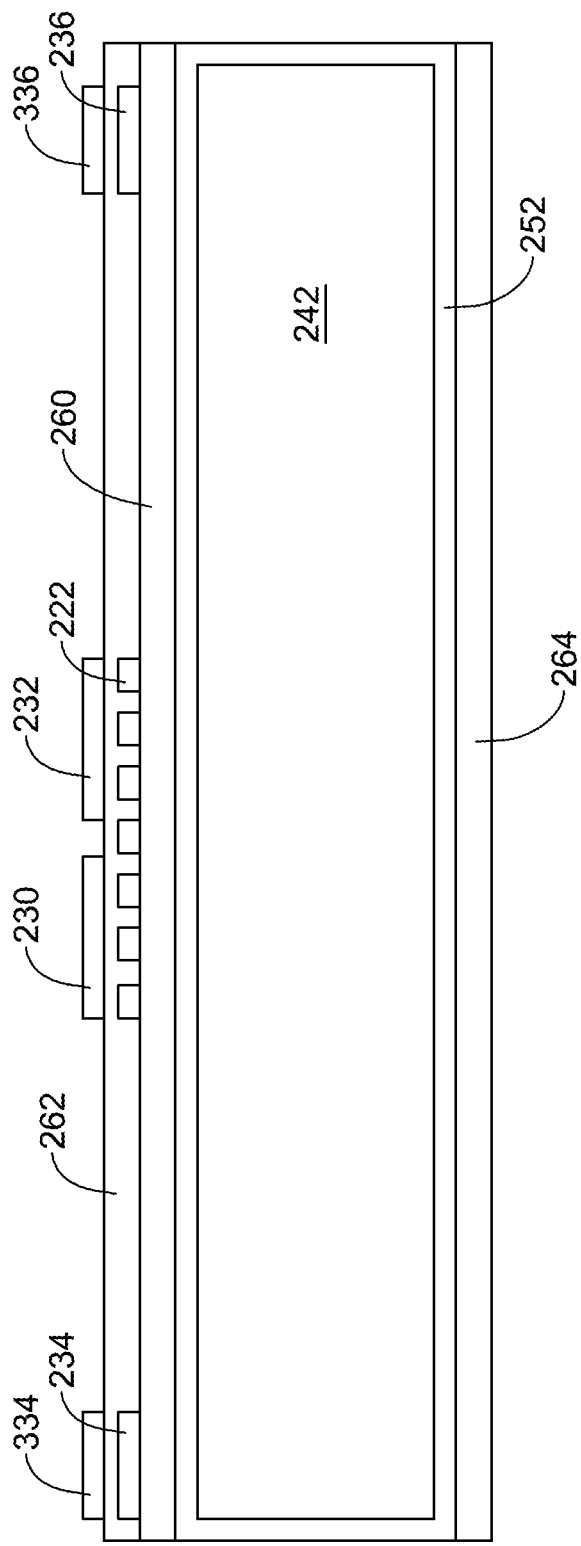

An insulating dielectric layer 262 may be provided over the resistive heater, as shown in FIG. 23. The insulating dielectric layer 262 may be formed of any suitable material, although in some embodiments, the insulating dielectric layer 262 includes or is otherwise formed of silicon dioxide or silicon nitride. In some embodiments, as shown in FIG. 24, a backside insulating dielectric layer 264 is also provided. A metal layer may be formed and patterned, as shown in FIG. 25, to form bond pads 334 and 336, as well as the first sensing electrode 230 and the second sensing electrode 232.

Figure 26:
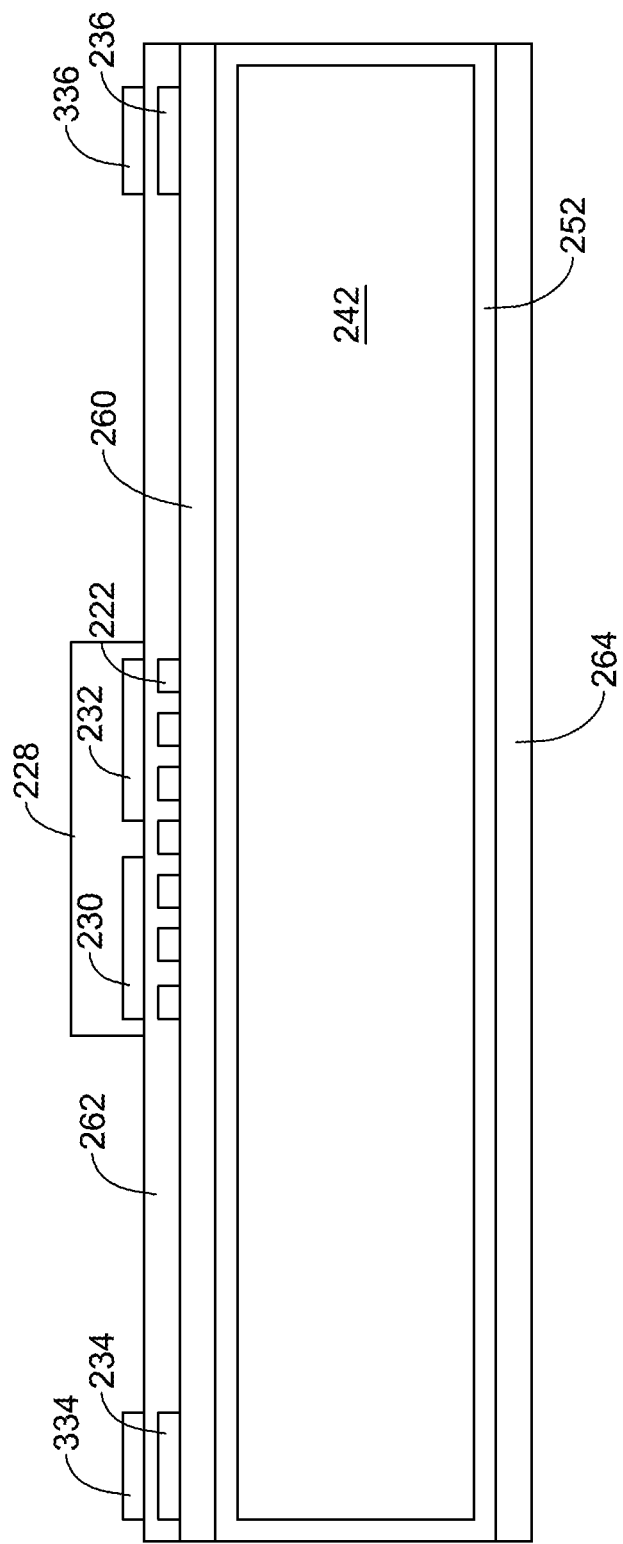

A sensing material 228 may be deposited, as shown in FIG. 26. The sensing material 228 may include a material, such as a polyimide, that has an electrical property that changes in response to changes in the moisture content of the sensing material 228. While not shown, a porous metal layer and/or protective polyimide cap may be disposed over the sensing material 228, if desired.

Figure 27:
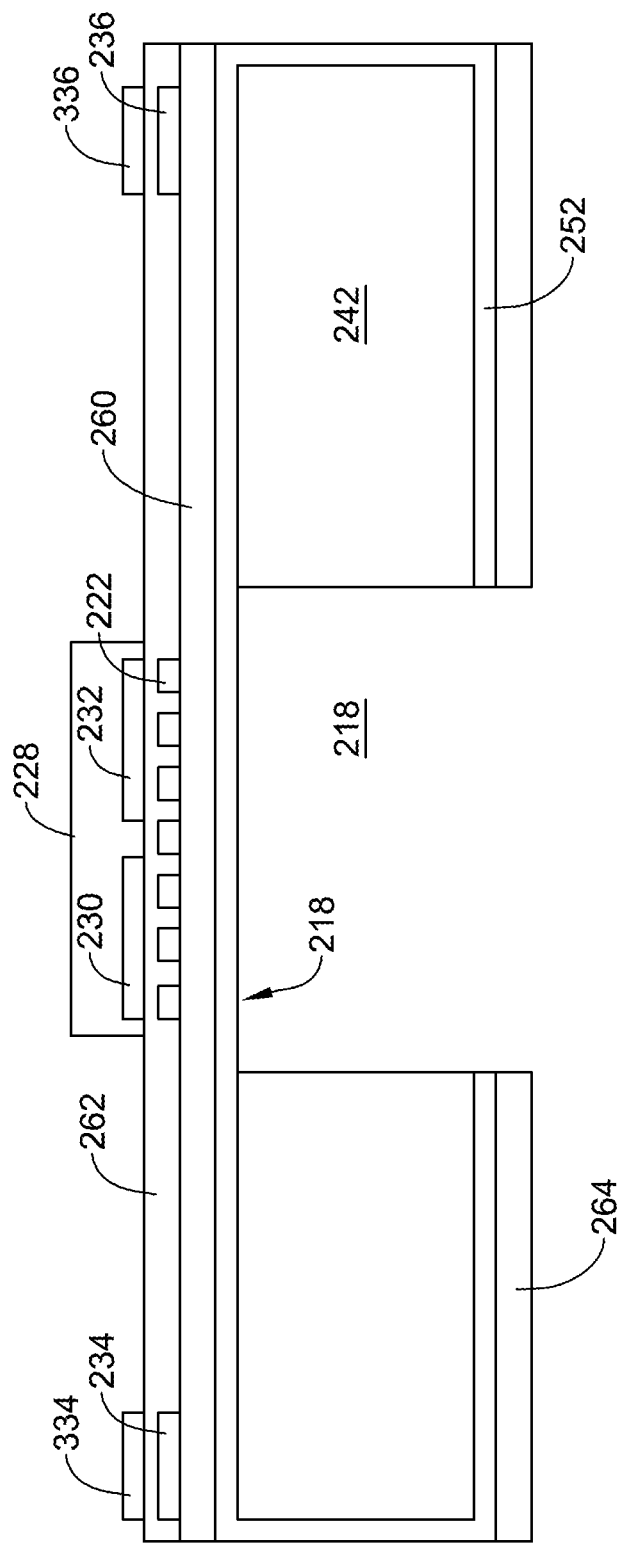

Turning to FIG. 27, the backside of the substrate 242 is patterned and etched to form the recess 218. In some cases, the oxide layer 252 may act as an etch stop, but this is not required. It will be appreciated that the recess 218 defines a diaphragm 220 that supports the sensing material 228, the sensing electrodes 230, 232 and the resistive heater element 222. In some embodiments, and as shown in FIG. 20, an insulating or low thermal conductivity material 264 may be deposited along the walls of the recess 218 to help thermally isolate the diaphragm 220 from the rest of the structure including the substrate 242, but this is not required. The insulating or low thermal conductivity material 264 may include materials such as polyimides, silica, aerogels including silica aerogel and xerogel, and the like.

The disclosure should not be considered limited to the particular examples described above. Various modifications, equivalent processes, as well as numerous structures to which the disclosure can be applicable will be readily apparent to those of skill in the art upon review of the instant specification.

What is claimed is:

1. A humidity sensor comprising:
a first substrate having a recess formed in a first side;
a second substrate;
an insulating layer supported by the second substrate;
the second substrate and the insulating layer supported by the first side of the first substrate and extending over the recess to form a diaphragm, with the insulating layer facing the recess;

a trench in the second substrate extending around or substantially around the diaphragm, the trench at least partially filled with an oxide to thermally insulate the diaphragm from a remainder of the second substrate;

a resistive heater element supported by the diaphragm;

a pair of sensing electrodes electrically separated from each other and supported by the diaphragm; and a sensing material disposed over the pair of sensing electrodes, wherein an electrical property of the sensing material is configured to change in response to a change in moisture content of the sensing material.

2. The humidity sensor of claim 1, further comprising a dielectric situated between the resistive heater element and the pair of sensing electrodes.

3. The humidity sensor of claim 1, wherein the pair of sensing electrodes comprises a first electrode plate situated laterally adjacent to a second electrode plate.

4. The humidity sensor of claim 1, wherein the pair of sensing electrodes comprises a first electrode, and a second electrode interdigitated with the first electrode.

5. The humidity sensor of claim 1, wherein the resistive heater element is configured to heat the sensing material sufficiently to dry the sensing material upon application of a current to the resistive heater element.

6. The humidity sensor of claim 1, further comprising a protective polyimide cap disposed over the sensing material.

7. The humidity sensor of claim 6, further comprising a porous metal layer disposed between the sensing material and the protective polyimide cap.

8. The humidity sensor of claim 1, wherein the trench in the second substrate does not overlap the recess in the first substrate.

9. The humidity sensor of claim 1, wherein the trench in the second substrate does overlap the recess in the first substrate.

10. A humidity sensor comprising:

a first silicon substrate having a recess formed in a first side;

a second silicon substrate;

an insulating layer supported by the second substrate;

the second silicon substrate and the insulating layer supported by the first side of the first silicon substrate and extending over the recess of the first silicon substrate to form a diaphragm, with the insulating layer facing the recess;

a trench in the second substrate circumscribing or substantially circumscribing the diaphragm;

a resistive heater element supported by the diaphragm;

a sensor electrode supported by the diaphragm; and a sensing layer disposed over the sensor electrode, wherein an electrical property of the sensing layer is configured to change in response to changes in moisture content of the sensing layer, wherein the trench does not extend through the insulating layer.

11. The humidity sensor of claim 10, wherein the trench in the second silicon substrate does not overlap the recess in the first silicon substrate.

12. The humidity sensor of claim 10, wherein the trench in the second silicon substrate does overlap the recess in the first silicon substrate.

13. The humidity sensor of claim 10, wherein the sensor electrode is part of a capacitance sensor.

14. The humidity sensor of claim 10, wherein the sensor electrode is part of a resistance sensor.

15. The humidity sensor of claim 10, further comprising a dielectric situated between the resistive heater element and the sensor electrode.

16. The humidity sensor of claim 10, further comprising a protective layer disposed over the sensing layer, with a porous metal layer disposed between the sensing layer and the protective layer.

* * * * *